(12) United States Patent
Hamann et al.

(10) Patent No.: US 9,340,346 B2
(45) Date of Patent: May 17, 2016

(54) PRECISION DISPENSING DEVICE OF SMALL VOLUME FROM PRE-FILLED SYRINGES

(71) Applicants: Curtis P. Hamann, Paradise Valley, AZ (US); Karl-Michael Klenk, Mesa, AZ (US); Bryan Richard Falk, Chandler, AZ (US)

(72) Inventors: Curtis P. Hamann, Paradise Valley, AZ (US); Karl-Michael Klenk, Mesa, AZ (US); Bryan Richard Falk, Chandler, AZ (US)

(73) Assignee: SmartHealth, Inc., Phoenix, AZ (US)

( * ) Notice: Subject to any disclaimer, the term of this patent is extended or adjusted under 35 U.S.C. 154(b) by 40 days.

(21) Appl. No.: 14/086,005

(22) Filed: Nov. 21, 2013

(65) Prior Publication Data

US 2015/0136809 A1    May 21, 2015

(51) Int. Cl.
*A61M 5/20* (2006.01)
*B65D 83/00* (2006.01)
*A61M 5/315* (2006.01)
(Continued)

(52) U.S. Cl.
CPC ........... *B65D 83/0033* (2013.01); *A61M 5/204* (2013.01); *A61M 5/31531* (2013.01); *A61M 5/28* (2013.01); *A61M 5/31593* (2013.01); *A61M 2005/3142* (2013.01)

(58) Field of Classification Search
CPC ...................... A61M 2005/2414; A61M 5/315; A61M 5/31525; A61M 5/3153; A61M 5/31531; A61M 5/31533; A61M 5/31555; A61M 5/31565; A61M 5/31576; A61M 5/31578; A61M 5/31593; A61M 5/3158

USPC ................ 222/252, 256, 260, 275, 278, 322, 222/325–327, 386
See application file for complete search history.

(56) References Cited

U.S. PATENT DOCUMENTS

| 960,081 A | * | 5/1910 | Fearon et al. | 222/256 |
| 1,587,597 A | * | 6/1926 | MaClellan | 222/340 |
| 1,686,309 A | * | 10/1928 | Zabriskie | 222/256 |

(Continued)

FOREIGN PATENT DOCUMENTS

| DE | 102013203782 | 9/2013 |
| EP | 0188032 A1 | 7/1986 |

(Continued)

OTHER PUBLICATIONS

U.S. Appl. No. 27/473,336, filed Nov. 21, 2013, Hamann et al.
(Continued)

*Primary Examiner* — Patrick M Buechner
(74) *Attorney, Agent, or Firm* — Reinhart Boerner Van Deuren P.C.

(57) ABSTRACT

A dispenser for dispensing a predetermined amount of material from a prefilled syringe. The dispenser includes a dispenser body and a plunger. The dispenser body includes a syringe mounting region and a nozzle portion through which the material is dispensed. The nozzle portion has a syringe dispensing end receiving cavity configured to mate with the dispensing end of the syringe and an outlet. A fluid flow path fluidly communicates the syringe dispensing end receiving cavity with the outlet and includes a measuring cavity having a predetermined volume. The plunger is carried by the dispenser body. The plunger has a retracted state in which the plunger is retracted from the measuring cavity such that the outlet is in fluid communication with the syringe dispensing end receiving cavity. The plunger has a depressed state in which the plunger extends through the measuring cavity to evacuate material from the measuring cavity.

20 Claims, 13 Drawing Sheets

(51) Int. Cl.
*A61M 5/28* (2006.01)
*A61M 5/31* (2006.01)

(56) References Cited

U.S. PATENT DOCUMENTS

| | | | | |
|---|---|---|---|---|
| 1,794,131 | A | * | 2/1931 | Zabriskie ..................... 222/256 |
| 1,926,495 | A | * | 9/1933 | Parker .......................... 222/256 |
| 1,926,496 | A | * | 9/1933 | Parker .......................... 222/256 |
| 2,515,956 | A | * | 7/1950 | Greenberg ................... 604/207 |
| 2,705,953 | A | | 4/1955 | Potez |
| 2,752,074 | A | * | 6/1956 | Martin ......................... 222/326 |
| 3,203,455 | A | | 8/1965 | Horabin |
| 3,819,091 | A | * | 6/1974 | Hollender .................... 222/327 |
| 3,978,846 | A | * | 9/1976 | Bailey .......................... 600/575 |
| 4,022,207 | A | * | 5/1977 | Citrin ........................... 604/209 |
| 4,189,065 | A | | 2/1980 | Herold |
| 4,312,343 | A | | 1/1982 | LeVeen et al. |
| 4,346,708 | A | | 8/1982 | LeVeen et al. |
| 4,583,978 | A | * | 4/1986 | Porat et al. .................. 604/208 |
| 4,643,724 | A | * | 2/1987 | Jobe ............................. 604/232 |
| 4,704,105 | A | * | 11/1987 | Adorjan et al. .............. 604/222 |
| 4,710,179 | A | | 12/1987 | Haber et al. |
| 4,810,249 | A | | 3/1989 | Haber et al. |
| 5,354,285 | A | * | 10/1994 | Mazurik et al. ............. 604/191 |
| 5,611,784 | A | * | 3/1997 | Barresi et al. ................ 604/211 |
| 2013/0126559 | A1 | * | 5/2013 | Cowan et al. ................ 222/333 |
| 2013/0245492 | A1 | | 9/2013 | Klenk et al. |

FOREIGN PATENT DOCUMENTS

| | | |
|---|---|---|
| EP | 0248760 A2 | 12/1987 |
| WO | WO 01/89613 A1 | 11/2001 |

OTHER PUBLICATIONS

U.S. Appl. No. 29/415,884, filed Mar. 15, 2012, Klenk et al.
Products. Datasheet [Online]. Diagenics LTD, [retrieved on Apr. 16, 2012]. Retrieved from the Internet: < URL: http://www.findtheneedle.co.uk/companies/diagenics-ltd.

* cited by examiner

US 9,340,346 B2

PRECISION DISPENSING DEVICE OF SMALL VOLUME FROM PRE-FILLED SYRINGES

FIELD OF THE INVENTION

This invention generally relates to the field of prefilled syringes. The present invention relates specifically to a dispensing device for dispensing fluid from a prefilled syringe.

BACKGROUND OF THE INVENTION

Prefilled syringes are used in a variety of areas, including for medical tests, therapeutic uses, and scientific uses. Prefilled syringes typically have a syringe body or syringe barrel and a plunger. The plunger includes a plunger head that seals to the inner surface of the syringe body forming a sealed cavity that holds a fluid, such as a medical test or therapeutic substance. The plunger includes a shaft coupled at one end to the plunger head, and at the other end, the shaft is coupled to a plunger top, sized to facilitate engagement by a user's finger or thumb. Pushing the plunger top forces the plunger head toward a dispensing opening located through the syringe body resulting in the dispensing or ejection of fluid or material from the syringe body.

The prefilled syringes may be used in many areas. For example, prefilled syringes may be used to hold allergen test substances. Typically, each prefilled syringe holds a volume of a single allergen test substance that may be used for multiple allergy tests for multiple patients. For example, such allergen test prefilled syringes may originally hold 5 milliliters of test substance. During an allergy test, a health care worker typically will dispense a small volume (e.g., less than 100 microliters) of test substance from the prefilled syringe into a receiving chamber that has been attached to the skin of a patient receiving an allergy test. The receiving chamber holds the allergen test substance in contact with the patient's skin, and the test area of skin is monitored for allergic reaction. Because only a small amount of the test substance is used for a single test, the prefilled syringe is used for multiple allergy tests for multiple patients. Unfortunately, it is often very difficult to accurately meter the amount of fluid or material being dispensed from the dispensing opening using the plunger of the syringe.

BRIEF SUMMARY OF THE INVENTION

One embodiment of the present invention provides a new and improved dispenser for use with and dispensing a predetermined volume of material from a prefilled syringe. More particularly, the syringe with which the dispenser works has a syringe body for storing the material and a syringe plunger mounted within the syringe body for pressing the material out of the syringe body through a dispensing end of the syringe which will have an outlet or dispensing opening.

The dispenser includes a dispenser body and a dispenser plunger. The dispenser body includes a syringe mounting region configured for receiving the syringe and a nozzle portion through which the material is dispensed. The nozzle portion has a syringe dispensing end receiving cavity configured to mate with the dispensing end of the syringe and an outlet. The nozzle portion defines a fluid flow path fluidly communicating the syringe dispensing end receiving cavity with the outlet. The outlet fluidly communicates the fluid flow path with the environment external to the nozzle portion of the dispenser. The fluid flow path includes a measuring cavity having a predetermined volume. The dispenser plunger is carried by the dispenser body. The dispenser plunger has a retracted state in which the dispenser plunger is retracted from the measuring cavity such that the outlet is in fluid communication with the syringe dispensing end receiving cavity. The dispenser plunger has a depressed state in which the dispenser plunger extends through the measuring cavity. The dispenser plunger evacuates material within the measuring cavity as the dispenser plunger transitions from the retracted state to the depressed state.

Preferably, the actuation of the dispenser plunger is entirely independent of the actuation of the syringe plunger and the actuation of the syringe plunger is entirely independent of the actuation of the dispenser plunger. Further, it is preferred that the motion of the plungers is generally along parallel and offset axes of motion.

In one embodiment, the plunger includes a tip portion having an outer peripheral shape and the measuring cavity has an inner peripheral shape that corresponds to the outer peripheral shape of the tip portion. Preferably, the corresponding shapes substantially provide a seal therebetween such that movement of the tip portion through the measuring cavity prevents fluid or material bypass while evacuating material from the measuring cavity.

In one embodiment, the outer peripheral shape of the tip portion is cylindrical or otherwise has a circular cross-section with a first diameter and the inner peripheral shape of the measuring cavity is cylindrical or otherwise has a circular cross-section with a second diameter. The first and second diameters being substantially identical such that a seal is provided therebetween. The second diameter may be slightly smaller than the first diameter so as to provide a friction fit therebetween, while being substantially identical. The second diameter could also be slightly larger and still be substantially identical. However, it should only be slightly smaller such that substantially no material remains within the measuring cavity after the transitioning motion from the retracted state to depressed state.

In one embodiment, the dispenser plunger includes a head portion that extends axially along a length of the dispenser plunger outward beyond a distal end of the dispenser body and is positioned adjacent the syringe plunger when a syringe is mounted within the syringe mounting region.

In one embodiment, the dispenser body includes a mounting arrangement configured to engage a cooperating mounting arrangement of a syringe when a syringe is mounted within the syringe mounting region. In a more particular embodiment, the mounting arrangement of the dispenser body is a recessed groove that receives a cooperating outward extending flange portion of the syringe body.

In one embodiment, the syringe dispensing end receiving cavity is configured to mate with the dispensing end of the syringe body to form a seal therebetween and prevent fluid bypass therebetween when a syringe is mounted to the dispenser body.

In one embodiment, the syringe dispensing end receiving cavity and the measuring cavity are laterally offset from one another and the fluid flow path includes a laterally extending connection portion fluidly connecting the measuring cavity with the syringe dispensing end receiving cavity.

In one embodiment, the nozzle portion includes a plunger cavity in fluid communication with the fluid flow path. The plunger cavity axially aligns with the measuring cavity (e.g. along the axis of motion of the dispenser plunger). The tip portion of the dispenser plunger is positioned within the plunger cavity in the retracted state. Preferably, the tip portion and the plunger cavity are sized and configured to provide a seal therebetween and prevent fluid or material bypass.

In another embodiment, a system for dispensing a predetermined volume of material from a prefilled syringe is provided. The system includes a prefilled syringe and anyone of the dispensers described above. In a particular embodiment, the syringe includes a syringe body for storing the material. The syringe also includes a syringe plunger mounted within the syringe body for pressing the material out of the syringe body through a dispensing end of the syringe. The dispenser includes a dispenser body and a dispenser plunger. The dispenser body includes a syringe mounting region configured for receiving the syringe and a nozzle portion. The nozzle portion has a syringe dispensing end receiving cavity configured to mate with the dispensing end of the syringe and an outlet. The nozzle portion defines a fluid flow path fluidly communicating the syringe dispensing end receiving cavity with the outlet. The outlet fluidly communicates the fluid flow path with the environment external to the nozzle portion. The fluid flow path includes a measuring cavity having a predetermined volume. The dispenser plunger is carried by the dispenser body. The dispenser plunger has a retracted state relative to the dispenser body in which the dispenser plunger is retracted from the measuring cavity such that the outlet is in fluid communication with the syringe dispensing end receiving cavity. The dispenser plunger has a depressed state relative to the dispenser body in which the dispenser plunger extends through the measuring cavity. The dispenser plunger evacuates material within the measuring cavity as the dispenser plunger transitions from the retracted state to the depressed state.

In one embodiment, the dispenser body includes a mounting arrangement configured to engage a cooperating mounting arrangement of the syringe when the syringe is mounted within the syringe mounting region to inhibit removal of the syringe from the syringe mounting region. The cooperating mounting arrangements affix the two components together. Typically, when the syringe is emptied, the entire system will be disposed of rather than reusing the dispenser.

In one embodiment, the mounting arrangement of the dispenser body is a recessed groove and the mounting arrangement of the syringe is an outward extending flange portion of the syringe body that is received in the recessed groove when the syringe is mounted to the dispenser.

In one embodiment, the syringe dispensing end receiving cavity is configured to mate with the dispensing end of the syringe body to form a seal therebetween and prevent fluid bypass therebetween.

A method of dispensing a predetermined amount of material is also provided. The method includes providing anyone of the various embodiments of a syringe and dispenser mentioned above. The method further includes actuating the syringe plunger to dispense material from the syringe body and through the fluid flow path until a portion of the material exits the outlet and to fill the measuring cavity with the dispenser plunger in the retracted state. To increase accuracy in the method, the portion of excess material that exits the outlet is preferably is removed prior to depressing the dispenser plunger. The method also includes depressing the dispenser plunger to transition the dispenser plunger from the retracted state to the depressed state to dispense the predetermined amount of the material from the measuring cavity.

Other aspects, objectives and advantages of the invention will become more apparent from the following detailed description when taken in conjunction with the accompanying drawings.

BRIEF DESCRIPTION OF THE DRAWINGS

The accompanying drawings incorporated in and forming a part of the specification illustrate several aspects of the present invention and, together with the description, serve to explain the principles of the invention. In the drawings.

While the invention will be described in connection with certain preferred embodiments, there is no intent to limit it to those embodiments. On the contrary, the intent is to cover all alternatives, modifications and equivalents as included within the spirit and scope of the invention as defined by the appended claims.

DETAILED DESCRIPTION OF THE INVENTION

Referring generally to the figures, a dispensing system configured to precisely dispense a predetermined amount of flowable material, such as a gel material is illustrated according to an embodiment. The dispensing system will typically include a dispenser configured to engage and work with prefilled syringes for dispensing the predetermined amount of material. The dispenser itself is typically a device separate from the prefilled syringe and is in the form of an attachment that attaches to the prefilled syringes and acts a metering device to provide higher degrees of incremental dispensing of the fluid contained within the prefilled syringes. A dispenser itself, independent of a syringe, may be an embodiment of the invention.

Figure 1:
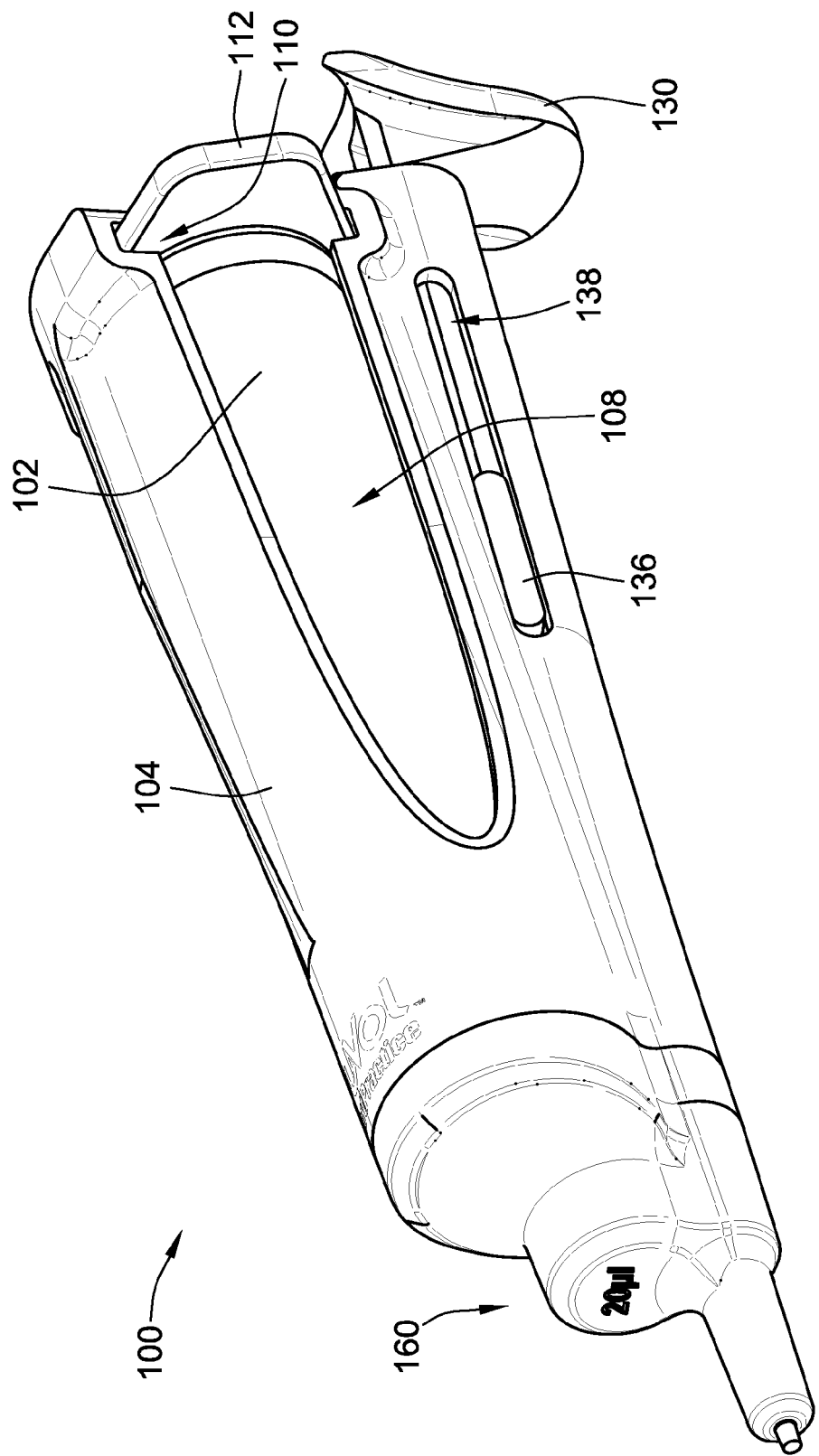
FIG. 1 is a perspective view of a dispensing system according to an embodiment of the present invention.
Figure 2:
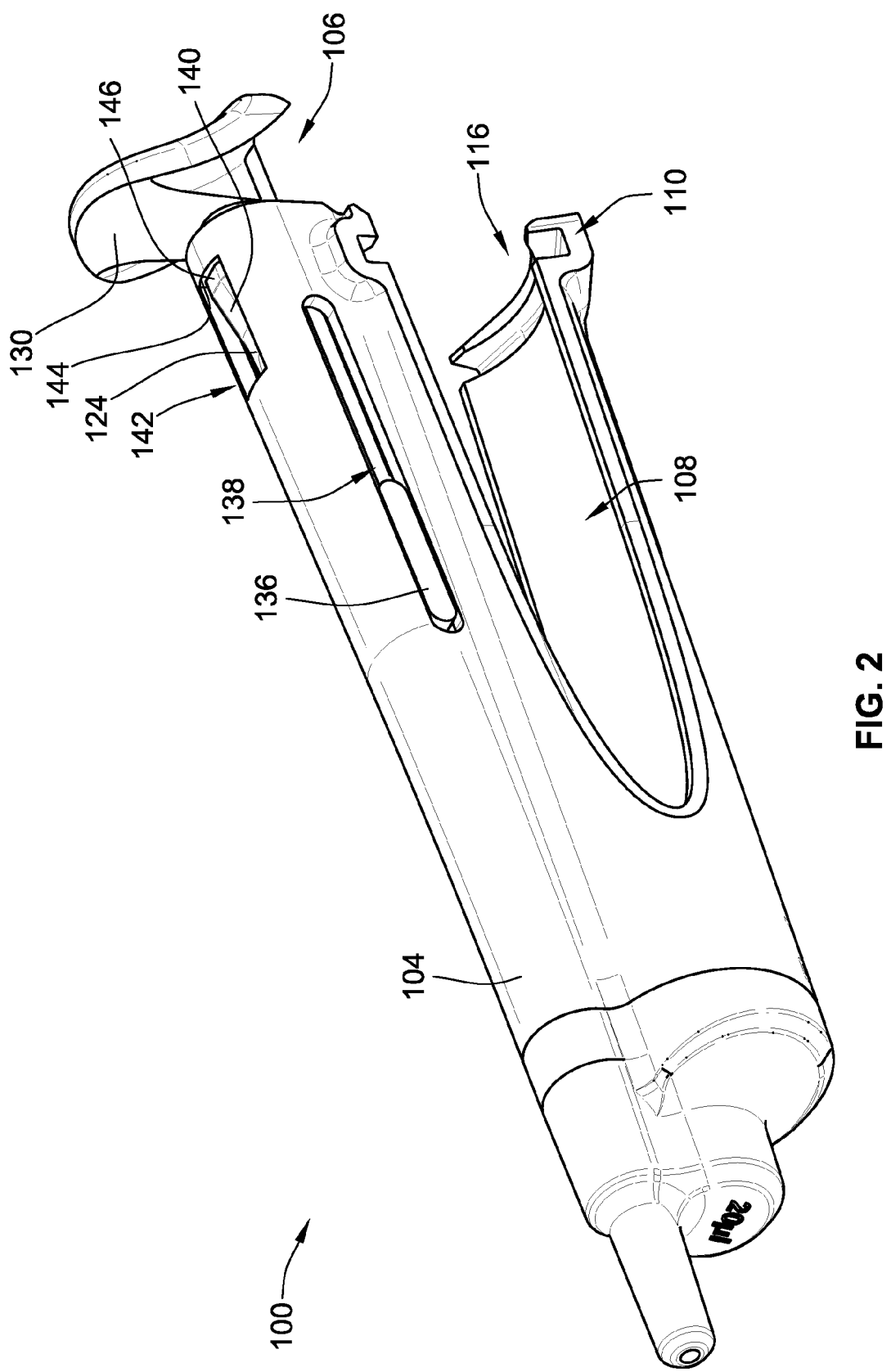
FIG. 2 is a perspective illustration of the dispenser of the dispensing system of FIG. 1.
Figure 3:
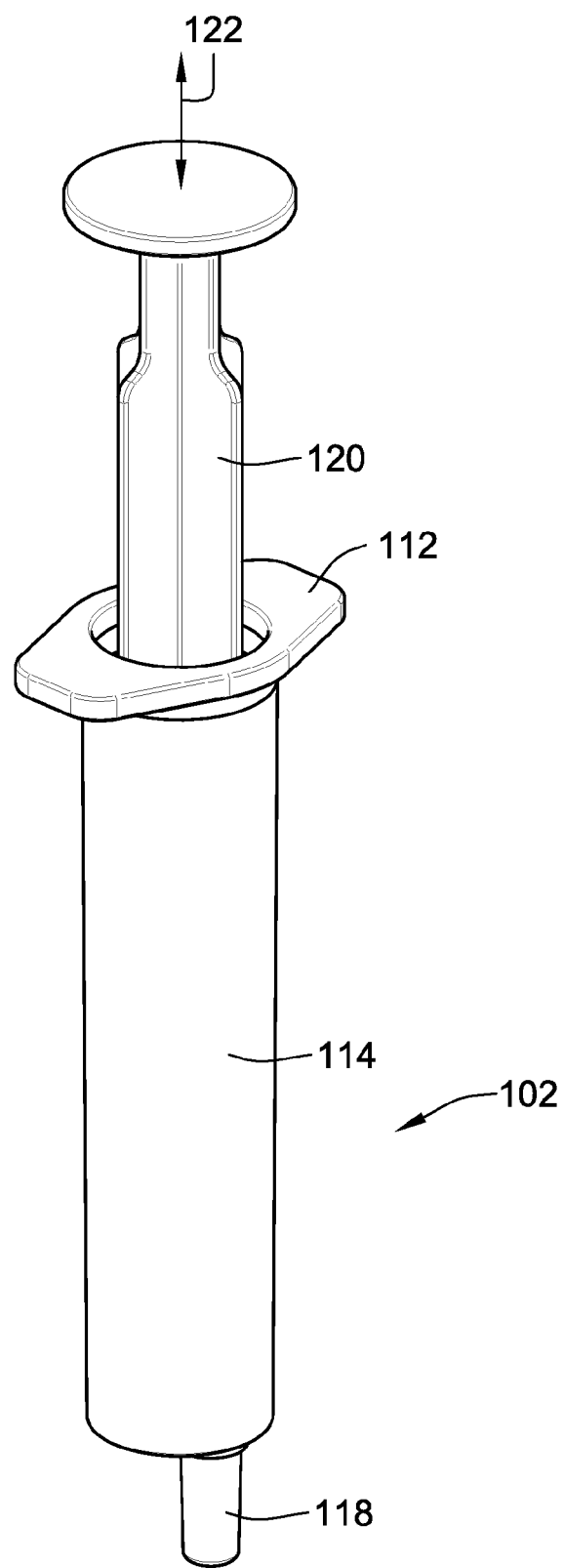
FIG. 3 is a simplified illustration of the syringe of the dispensing system of FIG. 1.
Figure 4:
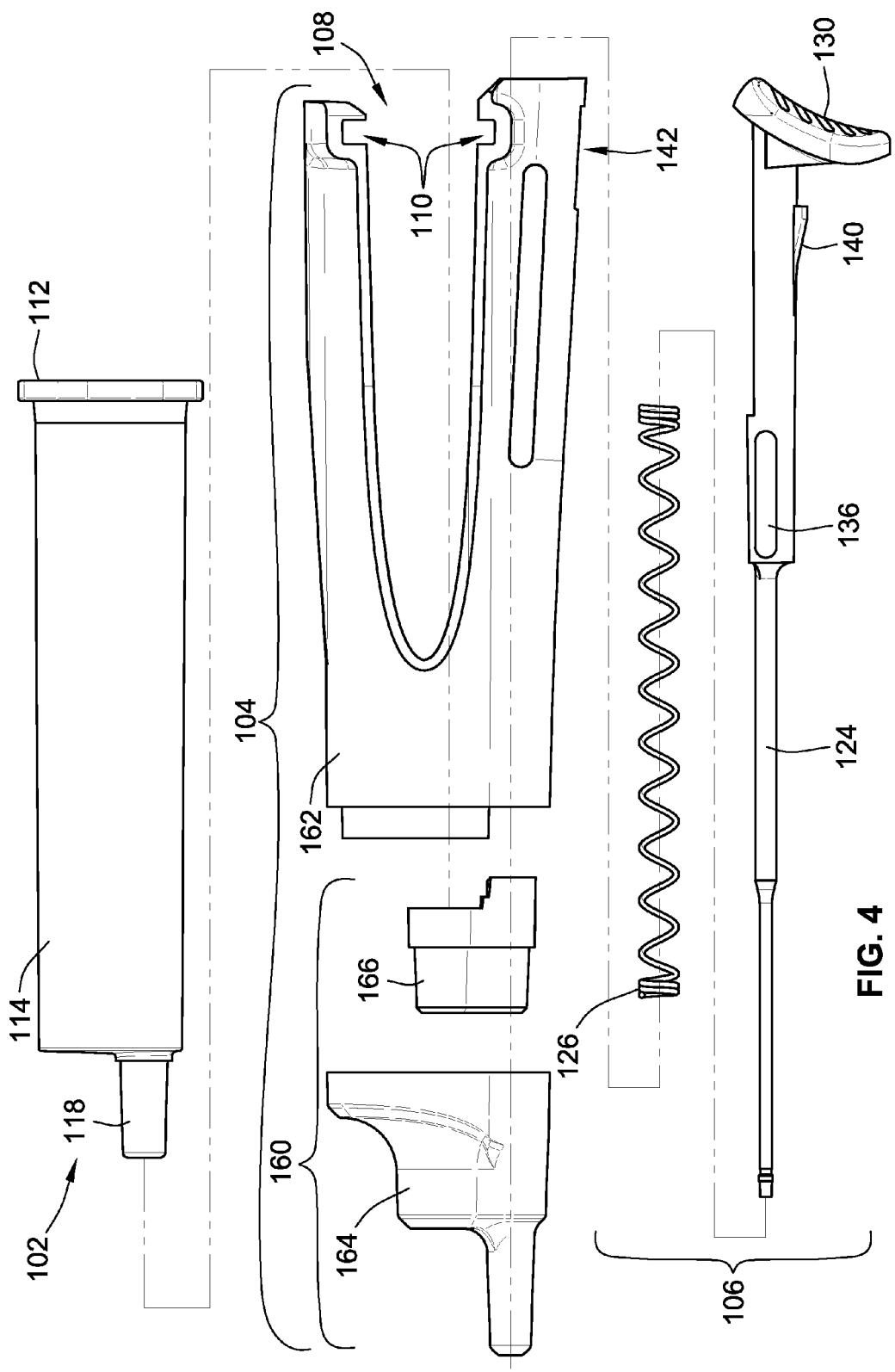
FIG. 4 is an exploded perspective illustration of the dispensing system of FIG. 1.
Figure 5:
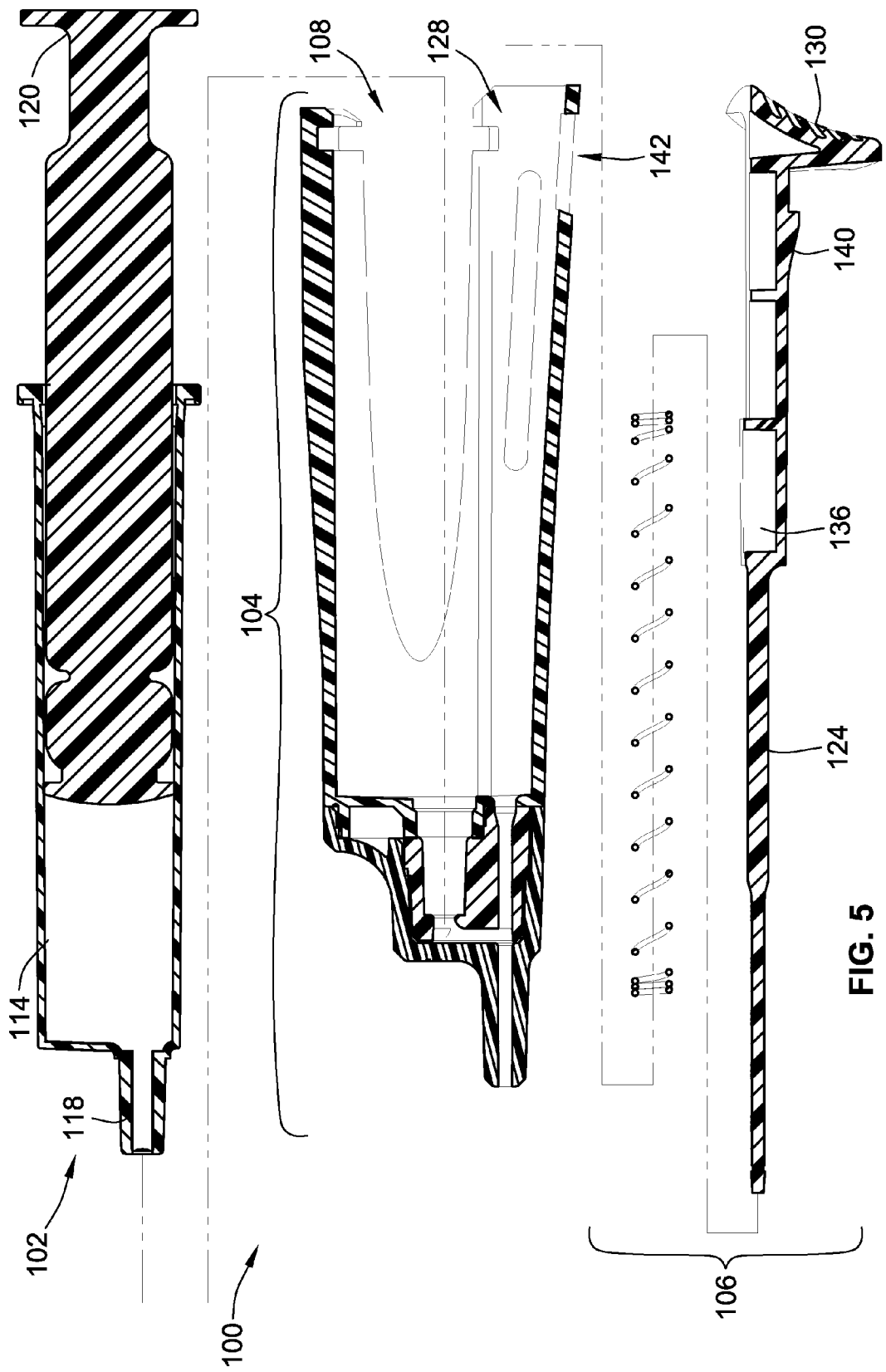
FIG. 5 is an exploded cross-sectional illustration of the dispensing system of FIG. 1.

FIGS. 1 and 2 illustrate a dispenser 100 configured to precisely dispense a volume of flowable material, such as a gel provided from a syringe 102 (see FIG. 3).

The dispenser 100 includes a dispenser body in the form of a dispenser body 104 that carries a plunger assembly 106 and which is configured to attach the dispenser to the syringe 102. The dispenser body 104 defines a mounting region 108, illustrated generally as a cavity, in which the syringe 102 is mounted during operation. The dispenser body 104 includes a mounting arrangement, in the form of mounting groove 110 configured to engage and mate with a cooperating mounting flange 112 of a syringe body 114 of the syringe 102. This mating engagement inhibits removal of the syringe from the mounting region 108. However, alternative embodiments of the mounting arrangement could be reversed where the dispenser body includes a projecting flange while the syringe body 114 could include a groove or recess to provide mating engagement therebetween.

The syringe 102 is received axially into the mounting region 108 through an open end 116 of the dispenser body 104. A dispensing end 118 is inserted first into the dispenser body 104 when mounting the syringe 102 within the mounting region 108. When the syringe 102 is mounted to the dispenser 100, the syringe plunger 120 is permitted to move freely axially into and out of the syringe body 114 illustrated generically by arrow 122.

With additional reference to FIGS. 4-7, the plunger assembly 106 in the illustrated embodiment generally includes a dispenser plunger 124 and a biasing member 126, illustrated in the form of a coil spring. The plunger assembly 106 is mounted in a plunger mounting channel 128 formed by the dispenser body 104 (see FIGS. 5-7). The dispenser plunger 124 is configured to slide axially within plunger mounting channel 128 so as to dispense material from the dispenser.

The plunger 124 includes a head portion 130 that extends axially out of the plunger mounting channel 128 and is actuatable by a user to press the dispenser plunger 124 axially into the plunger mounting channel 128 against force provided by the biasing member 126 that biases the dispenser plunger 124 axially out of the plunger mounting channel 128. With principle reference to FIG. 6, the biasing member 126 is axially compressed between an abutment surface 132 provided by the dispenser body 104 and another abutment surface 134 of the dispenser plunger 124 to bias the plunger 124 axially out of the plunger mounting channel 128.

With reference to FIG. 2, the dispenser plunger 124 includes a pair of guide flanges 136 (one shown) that extend radially outward and into corresponding guide slots 138 (one shown) formed in the dispenser body 104 adjacent the plunger mounting channel 128. The guide flanges 136 limit the axial motion of the dispenser plunger 124 axially within the plunger mounting channel 128 during normal operation. It is noted that the guide flanges 136 and/or dispenser body 104 are configured to allow the guide flanges 136 to slide past the dispenser body 104 by applying larger than normal force to allow for assembly of the dispenser 100.

Figure 6:
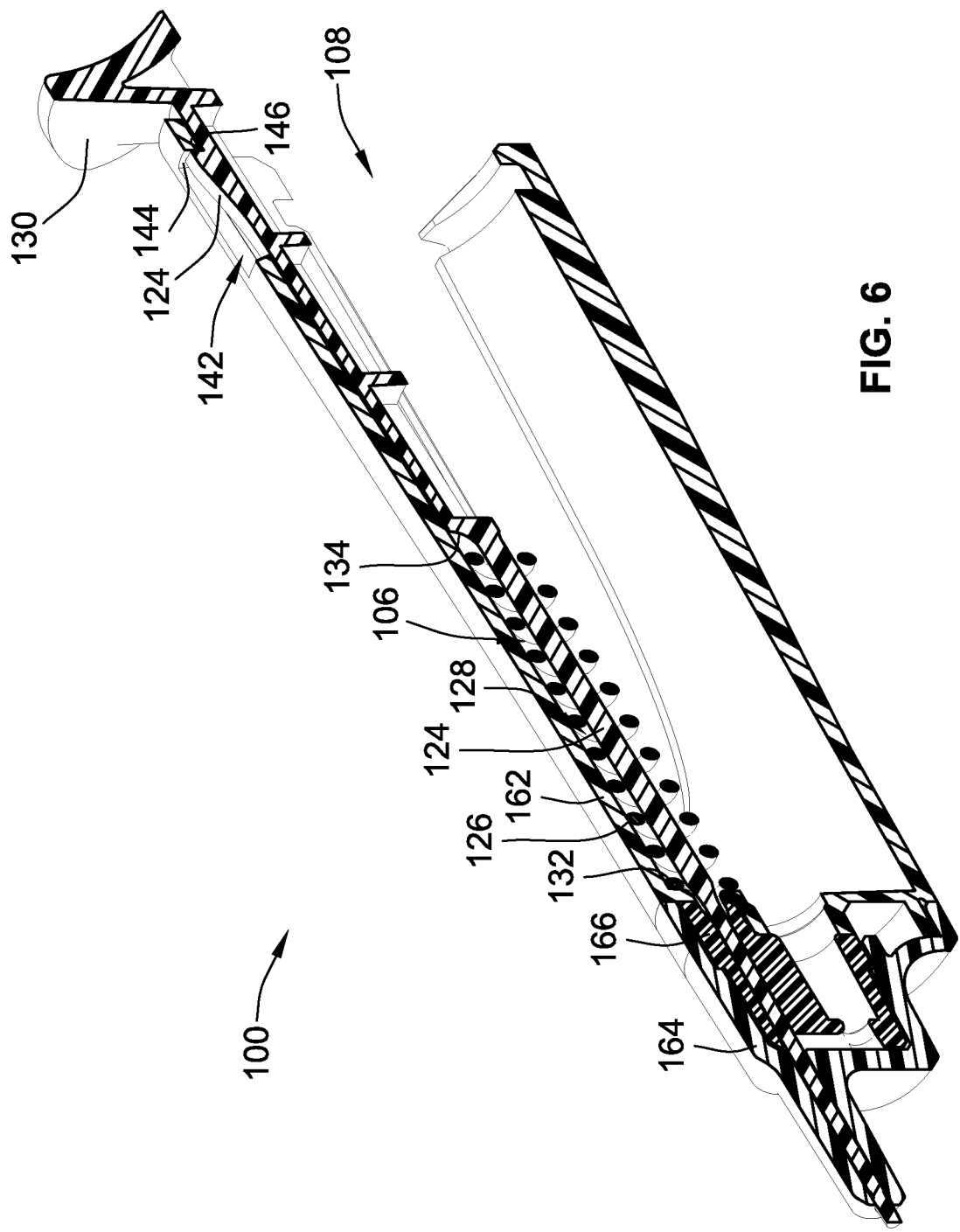
FIG. 6 is an assembled cross-sectional illustration of the dispensing system with the dispenser plunger in a depressed state.
Figure 7:
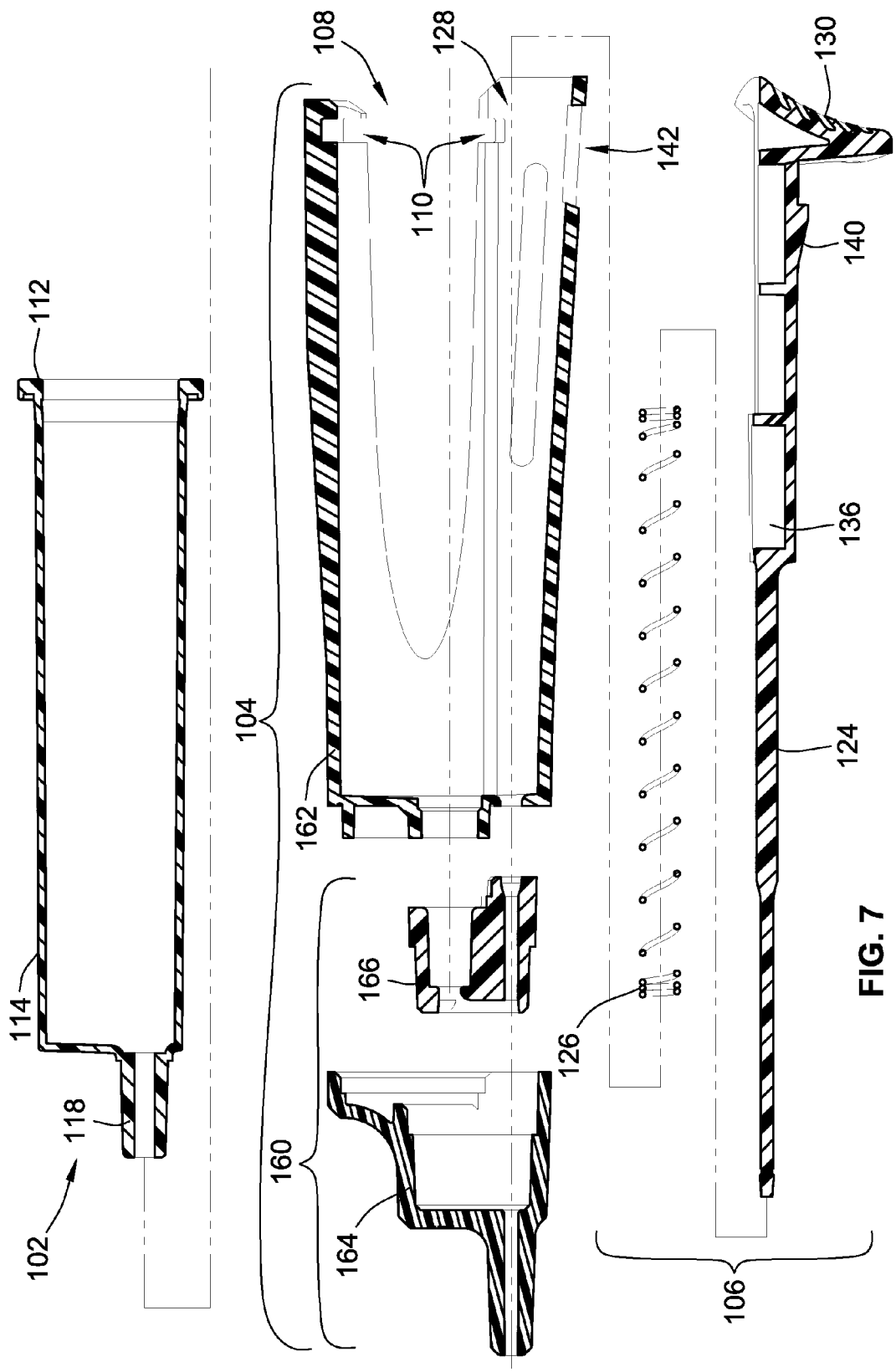
FIG. 7 is a further exploded cross-sectional illustration of the dispensing system of FIG. 1.

With reference to FIGS. 2 and 6, the dispenser plunger 124 and dispenser body 104 have a cooperating catch arrangement provided by a radially outward extending catch 140 provided by the dispenser plunger 124 and a catch slot 142 provided by the dispenser body 104. The catch slot 142 provides a stop 144 that cooperates with a catch abutment surface 146 to inhibit ejection of the dispensing plunger 124 from the plunger mounting channel 128 when the dispenser plunger 124 has been axially pressed into the dispenser body 104.

Figure 8:
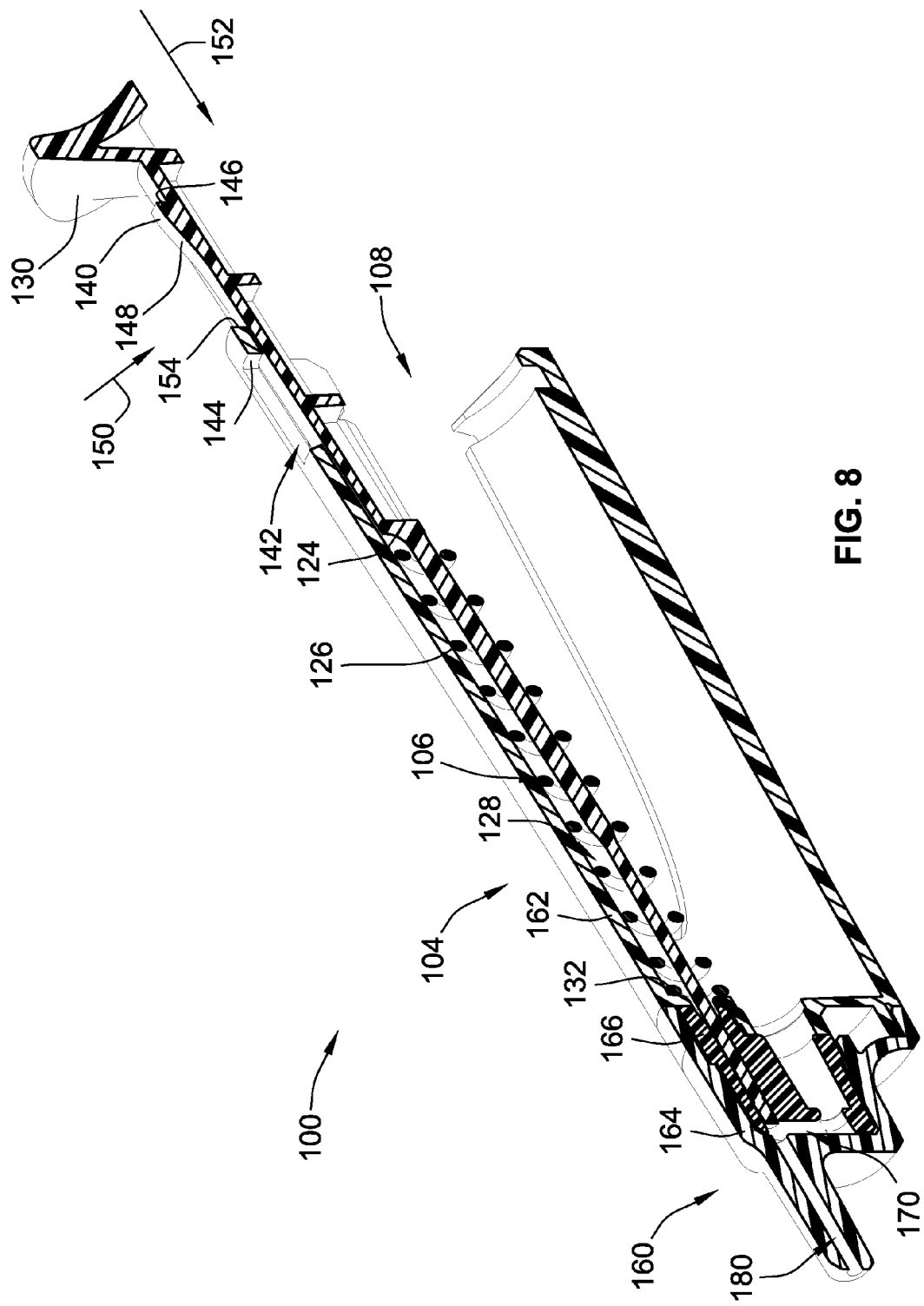
FIG. 8 is an assembled cross-sectional illustration of the dispenser of FIG. 1 with the dispenser plunger in a retracted state.

However, the dispenser plunger 124 is designed to flex radially inward, (e.g. toward the syringe mounting region 108) so as to remove the catch 140 from the catch slot 142 to allow the dispenser plunger 124 to be more fully ejected from the plunger mounting channel 128. This second state is illustrated in FIG. 8 with the dispenser plunger 124 fully ejected. Typically, the user will push radially inward, illustrated by arrow 150, on the head portion 130 to disengage the stop 144 and catch abutment surface 146 and allow for ejection.

The guide flanges 136 and guide slots 138 provide a second cooperating catch arrangement to limit the amount of ejection of the dispenser plunger 124 when the stop 144 and the catch abutment surface 146 are disengaged so as to prevent fully ejecting the dispenser plunger 124 from the dispenser body 124, and particularly plunger mounting channel 128, during normal operation.

The catch 140 includes a ramped surface 148 that assists in flexing the dispenser plunger 124 radially inward, illustrated by arrow 150, when the dispenser plunger 124 is pressed axially inward into the plunger mounting channel 128, illustrated by arrow 152. The ramped surface 148 will contact and slide against free end 154 of the dispenser body 104 to bias the head portion 130 of the dispenser plunger 124 radially inward.

Figure 9:
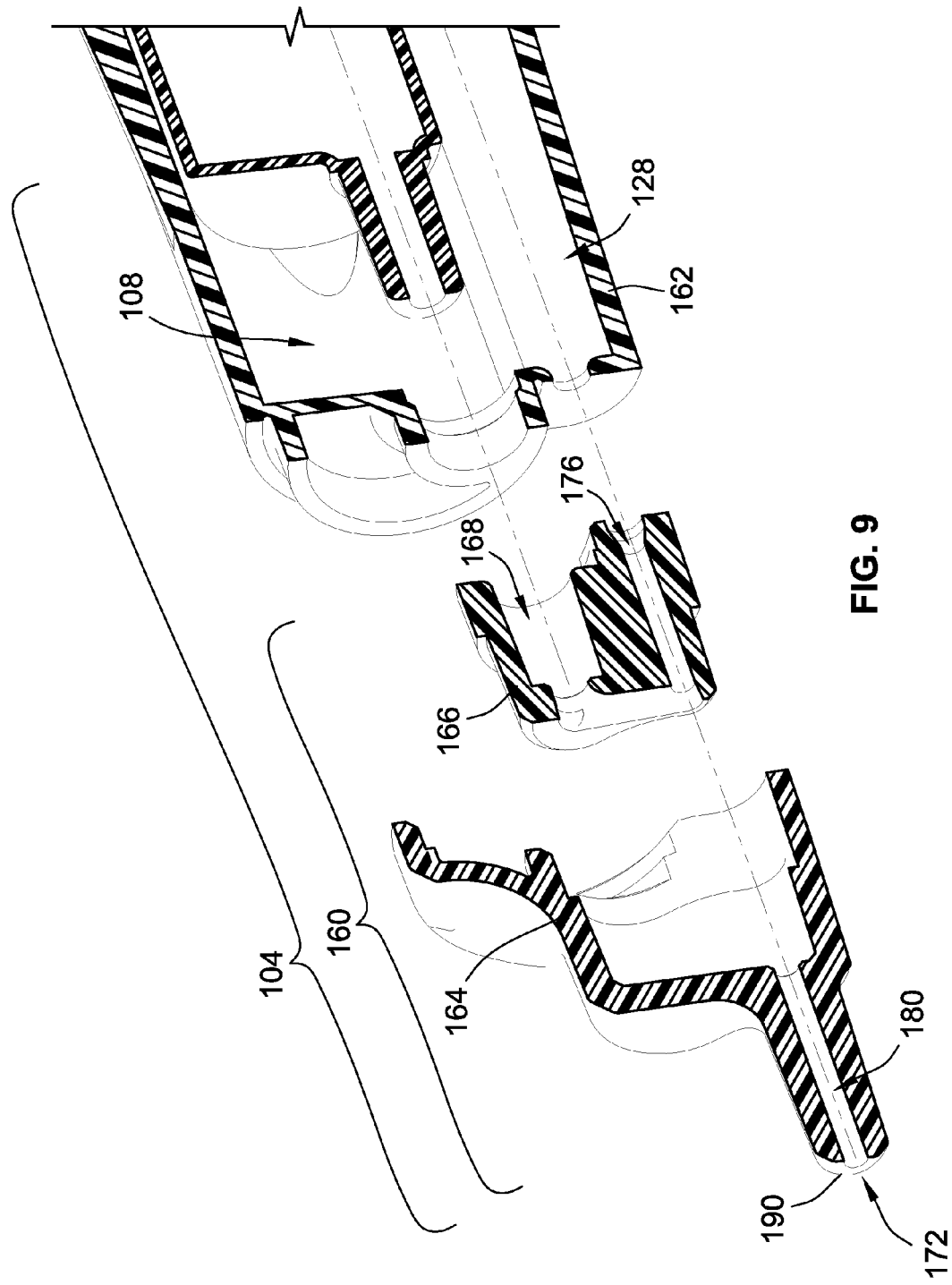
FIG. 9 is an enlarged cross-sectional and exploded illustration of the nozzle portion of the dispenser body of the dispenser of FIG. 1.
Figure 10:
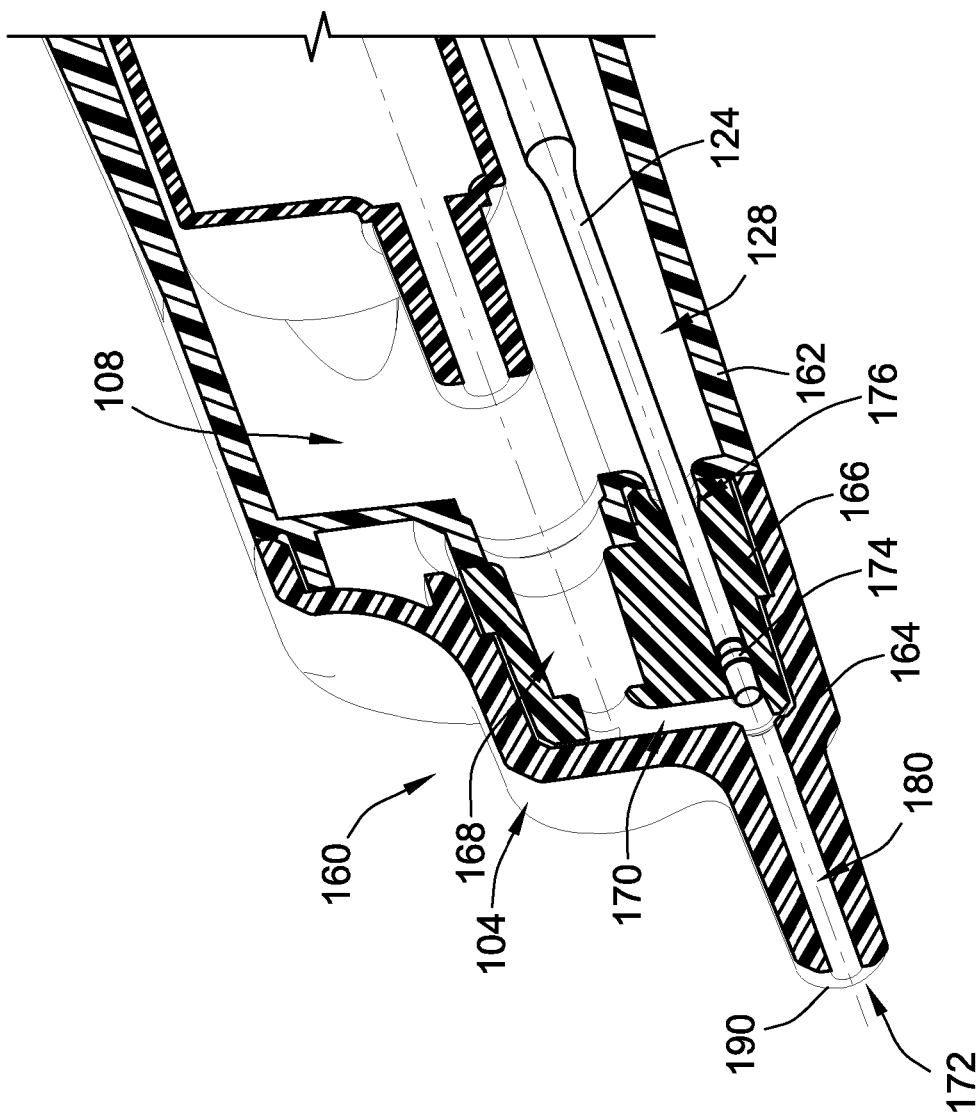
FIG. 10 is an enlarged cross-sectional illustration of the nozzle portion of the dispenser of FIG. 1 with the dispenser plunger in a retracted state.

With reference to FIGS. 9 and 10, the dispenser body 104, in the illustrated embodiment, is an assembly formed form a plurality of components assembled into a unitary construction. The dispenser body 104 includes a nozzle assembly 160 that becomes permanently attached, typically by welding, and more particularly by ultrasonic or spin welding, to a main body portion 162. The nozzle assembly 160 includes a nozzle portion 164 and a plug portion 166. The nozzle portion 164 and plug portion 166 are preferably permanently attached to one another, typically by welding, and more particularly by ultrasonic or spin welding. The use of welding helps avoid introduction of non-compatible materials to the dispenser 100 that may come in contact with the material that is dispensed from a particular syringe 102.

The nozzle assembly 160 includes a receiving cavity 168 for receiving the dispensing end 118 of syringe 102 (see e.g. FIGS. 11 and 12), which, in this embodiment, is provided by the plug portion 166. The receiving cavity 168 is matched to mate with the dispensing end 118 of syringe 102 so as to provide a seal therebetween to prevent fluid bypass back into the syringe mounting region 108 of the dispenser body 104. Preferably, the inner dimensions of the receiving cavity 168 are equal to or slightly smaller than the outer corresponding dimensions of the dispensing end 118 of the syringe body 114 so that a friction fit is provided therebetween and to provide a seal. Typically, these components will have a cylindrical or circular cross-section.

Figure 12:
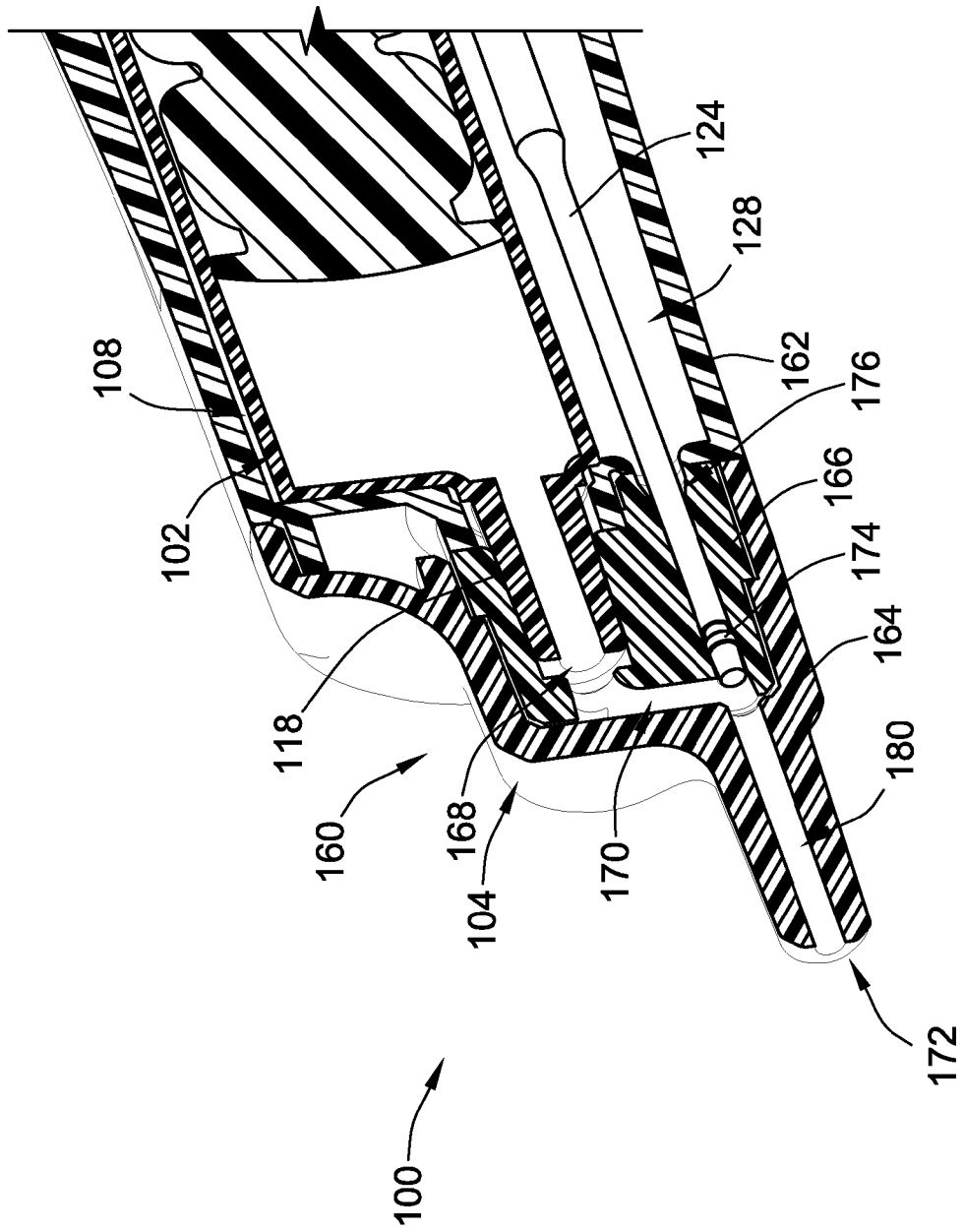
FIG. 12 is an enlarged cross-sectional illustration of the system of FIG. 1 with the dispenser plunger in a retracted state.

With reference to FIGS. 10 and 12, the nozzle assembly 160 defines a material flow path 170 through the nozzle portion 164 and the plug portion 166. The material flow path begins in the receiving cavity 168 and exits at outlet 172 of the nozzle portion 164.

When the dispenser plunger 124 is in an ejected state or released state, see e.g. FIG. 8 and FIG. 12, the fluid flow path 170 through the nozzle assembly 160 is open. In the open state, the dispenser plunger 124 is retracted from the fluid flow path 170 such that fluid with in the syringe 102 can be dispensed from the dispenser 100 by actuating the syringe plunger 120. When the dispenser plunger 124 is in this ejected or released state, the tip portion 174 of the dispenser plunger 124 is retracted into a plunger cavity 176 of the nozzle assembly 160 and particularly of the plug portion 166. The outer diameter of the tip portion 174 and the inner diameter of the plunger cavity 176 are sized to prevent fluid bypass back into the plunger mounting channel 128 in this state. The tip portion 174 may have a tapered end to facilitate sliding of the dispenser plunger 124. Similarly, the plunger cavity 176 may have a tapered lead-in section to facilitate insertion of the dispenser plunger 124 during assembly. Typically, the tip portion 174 will have a circular cross-section.

Figure 11:
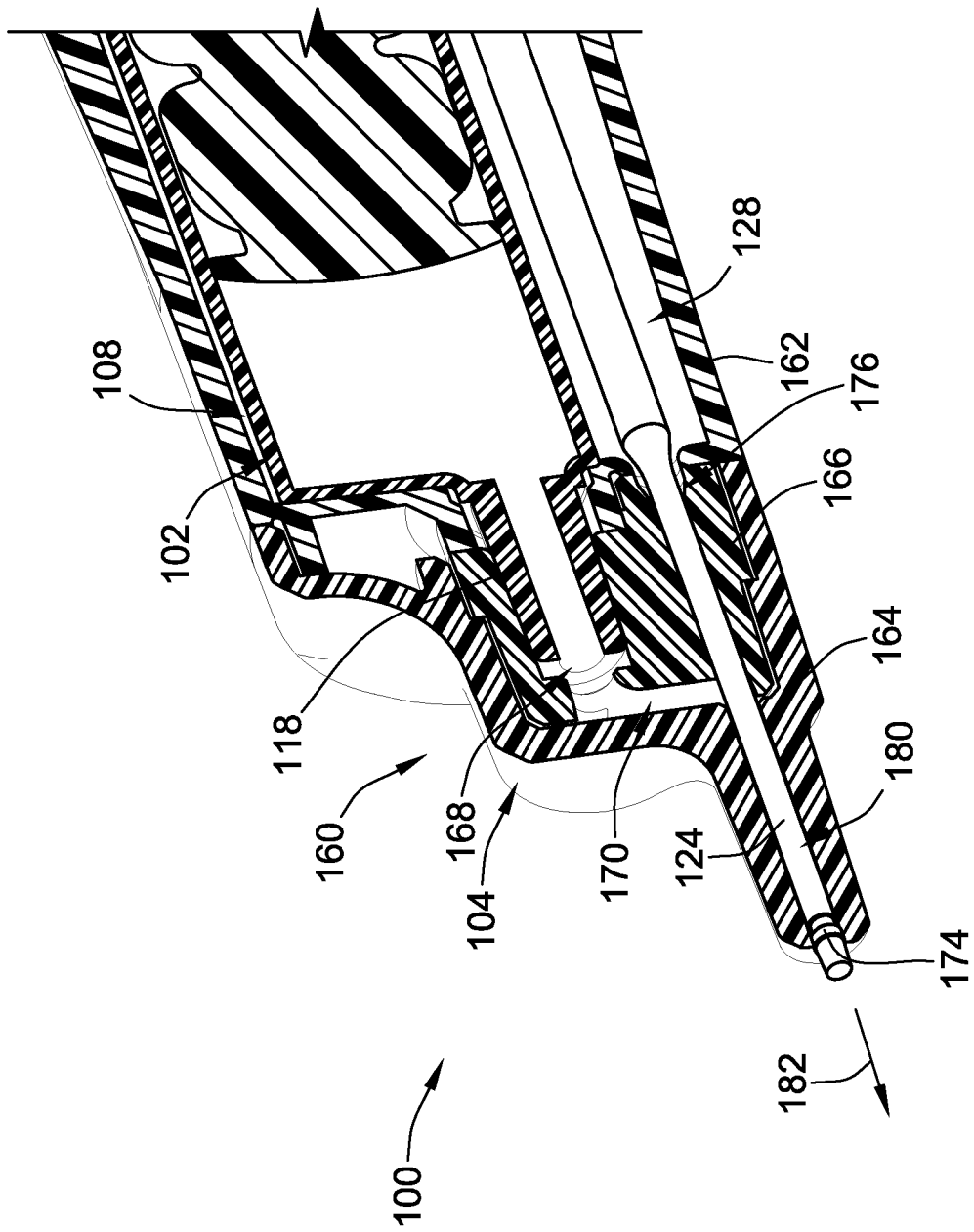
FIG. 11 is an enlarged cross-sectional illustration of the nozzle portion of the dispenser of FIG. 1 with the dispenser plunger in a depressed state.

When the dispenser plunger 124 is in a depressed or locked state, see e.g. FIGS. 6 and 11, the fluid flow path 170 through the nozzle assembly 160 is blocked and closed. In the blocked or closed state, the dispenser plunger 124 extends into the fluid flow path 170 such that fluid cannot be dispensed from the dispenser 100 when the syringe plunger 120 is actuated. With reference to FIG. 11, when the dispenser plunger 124 is in this depressed state, the tip portion 174 of the dispenser plunger 124 is inserted into a measuring cavity 180 of the nozzle assembly 160 and particularly of the nozzle portion 164. The measuring cavity 180 forms part of the fluid flow path 170. The outer diameter of the tip portion 174 and the inner diameter of the measuring cavity 180 are sized to prevent fluid as the tip portion 174 travels axially through the measuring cavity 180, illustrated by arrow 182 such that any fluid within the measuring cavity 180 is pushed out of the measuring cavity 180 by the tip portion 174.

The dispenser plunger and the measuring cavity 180 are sized and configured relative to one another such that each time the dispenser plunger 124 passes through the measuring cavity 180 a precise predetermined amount of fluid is dispensed from the dispenser 100.

To operate the dispenser 100, a user would first attach the dispenser 100 to a syringe 102, preferably a prefilled syringe. The user will engage mounting flange 112 with mounting groove 110 to secure the syringe 102 within the dispenser 100. In doing so, the user will also introduce the dispensing end 118 of the syringe 102 into the receiving cavity 168 of the nozzle assembly 160.

The user would then retract or release the dispenser plunger 124, if not already retracted to the released state illustrated in FIG. 8. This opens the fluid flow path 170 as illustrated in FIGS. 8 and 12.

Figure 13:
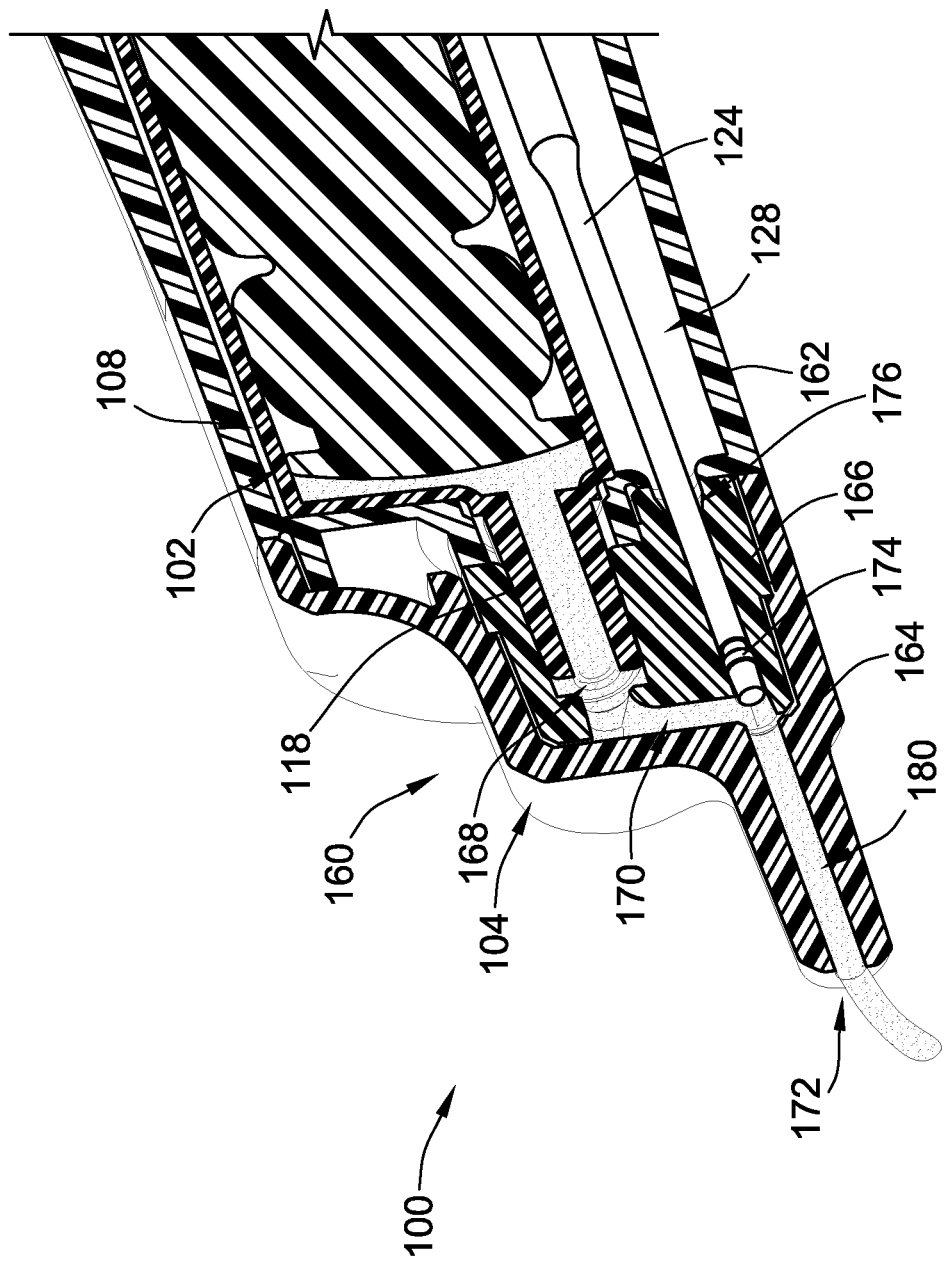
FIG. 13 is an enlarged cross-sectional illustration of the system of FIG. 1 showing material being biased out of the outlet of the nozzle portion of the dispenser of FIG. 1.

The user would then depress the syringe plunger 120 until fluid stored within the syringe 102 flows through and fills the fluid flow path 170 and exits the outlet 172 of the nozzle assembly 160 as illustrated in FIG. 13. At this stage, the measuring cavity 180 of the nozzle assembly 160 is filled with fluid. Typically, the fluid or material will be in a gel like state such that it will not simply drip or run out of the dispenser 100. The user will remove the excess material that is extending out from the distal end 190 of the nozzle portion 164 such that the material is flush with the distal end 190.

The user will then fully depress the dispenser plunger 124 and compress biasing member 126 by pressing on head portion 130. At this time, the catch 140 will insert into the catch slot 142 to prevent ejection of the dispenser plunger 124 from the plunger mounting channel 128. As the dispenser plunger 124 is depressed, the tip portion 174 will enter into and pass through the measuring cavity 180 dispensing the material therein through outlet 172.

The close fit between the inner peripheral shape of the inner surface defining the measuring cavity 180 and the outer peripheral shape of the outer surface of the tip portion 174 provides a good dispensing action of the material. The fit between tip portion 174 and the measuring cavity 180 also provides a seal preventing further fluid to be dispensed from the outlet 172 in the event that the syringe plunger 120 is further depressed.

If a further quantity of material is desired to be dispensed. The user will release the dispenser plunger 124, and particularly the cooperating catch arrangement, to eject the dispenser plunger 124 to its released state. Thereafter, the user can again depress the syringe plunger 120 until another portion of material/fluid is dispensed from the outlet 172.

Because the dispenser 100 comes in contact with the fluid within the syringe, the dispenser 100 will typically not be reused. As such, once the syringe 102 is emptied, the entire dispensing system, i.e. dispenser 100 and syringe 102, is discarded.

All references, including publications, patent applications, and patents cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) is to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A dispenser for use with and dispensing a predetermined volume of material from a prefilled syringe, the syringe having a syringe body for storing the material and a syringe plunger mounted within the syringe body for pressing the material out of the syringe body through a dispensing end of the syringe, the dispenser comprising:
 a dispenser body including:
  a syringe mounting region configured for receiving the syringe;
  a nozzle portion having a syringe dispensing end receiving cavity configured to mate with the dispensing end of the syringe and an outlet, the nozzle portion defining a fluid flow path fluidly communicating the syringe dispensing end receiving cavity with the outlet, the outlet fluidly communicating the fluid flow path with the environment external to the nozzle portion, the fluid flow path including a measuring cavity having a predetermined volume; and
 a dispenser plunger carried by the dispenser body having a retracted state in which the dispenser plunger is retracted from the measuring cavity such that the outlet is in fluid communication with the syringe dispensing end receiving cavity and a depressed state in which the dispenser plunger extends through the measuring cavity, the dispenser plunger evacuating material within the measuring cavity as the dispenser plunger transitions from the retracted state to the depressed state; and wherein the dispenser plunger includes a tip portion that extends through the measuring cavity and out of the outlet in the depressed state.

2. The dispenser of claim 1, wherein the dispenser plunger includes a head portion that extends axially outward beyond a distal end of the dispenser body and is positioned adjacent the syringe plunger when a syringe is mounted within the syringe mounting region.

3. The dispenser of claim 1, wherein the syringe dispensing end receiving cavity is configured to mate with the dispensing end of the syringe body to form a seal therebetween and prevent fluid bypass therebetween, when a syringe is mounted to the dispenser body.

4. The dispenser of claim 1, wherein the dispenser body includes a mounting arrangement configured to engage a cooperating mounting arrangement of a syringe when a syringe is mounted within the syringe mounting region.

5. The dispenser of claim 4, wherein the mounting arrangement of the dispenser body is a recessed groove that receives a cooperating outward extending flange portion of the syringe body.

6. The dispenser of claim 1, wherein the syringe dispensing end receiving cavity and the measuring cavity are laterally offset from one another and the fluid flow path includes a laterally extending connection portion fluidly connecting the measuring cavity with the syringe dispensing end receiving cavity.

7. The dispenser of claim The dispenser of claim 6, wherein the nozzle portion includes a plunger cavity that is laterally offset from the syringe dispensing end receiving cavity, the plunger cavity in fluid communication with the fluid flow path, the plunger cavity axially aligned with the measuring cavity, the tip portion of the dispenser plunger being positioned within the plunger cavity in the retracted state.

8. The dispenser of claim 1, wherein the plunger includes a tip portion having an outer peripheral shape and the measuring cavity has an inner peripheral shape that corresponds to the outer peripheral shape of the tip portion.

9. The dispenser of claim 8, wherein the outer peripheral shape of the tip portion is cylindrical with a first diameter and the inner peripheral shape of the measuring cavity is cylindrical with a second diameter, the first and second diameters being substantially identical.

10. The dispenser of claim 8, wherein the nozzle portion includes a plunger cavity in fluid communication with the fluid flow path, the plunger cavity axially aligned with the measuring cavity, the tip portion of the dispenser plunger being positioned within the plunger cavity in the retracted state.

11. A system for dispensing a predetermined volume of material from a prefilled syringe, the system comprising:
a prefilled syringe including:
a syringe body for storing the material; and
a syringe plunger mounted within the syringe body for pressing the material out of the syringe body through a dispensing end of the syringe;
a dispenser comprising:
a dispenser body including:
a syringe mounting region configured for receiving the syringe;
a nozzle portion having a syringe dispensing end receiving cavity configured to mate with the dispensing end of the syringe and an outlet, the nozzle portion defining a fluid flow path fluidly communicating the syringe dispensing end receiving cavity with the outlet, the outlet fluidly communicating the fluid flow path with the environment external to the nozzle portion, the fluid flow path including a measuring cavity having a predetermined volume; and a dispenser plunger carried by the dispenser body having a retracted state in which the dispenser plunger is retracted from the measuring cavity such that the outlet is in fluid communication with the syringe dispensing end receiving cavity and a depressed state in which the dispenser plunger extends through the measuring cavity, the dispenser plunger evacuating material within the measuring cavity as the dispenser plunger transitions from the retracted state to the depressed state; and wherein the dispenser plunger includes a tip portion that extends through the measuring cavity and out of the outlet in the depressed state.

12. The system of claim 11, wherein the syringe dispensing end receiving cavity is configured to mate with the dispensing end of the syringe body to form a seal therebetween and prevent fluid bypass therebetween.

13. The system of claim 11, wherein the dispenser body includes a mounting arrangement configured to engage a cooperating mounting arrangement of the syringe when the syringe is mounted within the syringe mounting region to inhibit removal of the syringe from the syringe mounting region.

14. The system of claim 13, wherein the mounting arrangement of the dispenser body is a recessed groove and the mounting arrangement of the syringe is an outward extending flange portion of the syringe body that is received in the recessed groove when the syringe is mounted to the dispenser.

15. The dispenser of claim 11, wherein the syringe dispensing end receiving cavity and the measuring cavity are laterally offset from one another and the fluid flow path includes a laterally extending connection portion fluidly connecting the measuring cavity with the syringe dispensing end receiving cavity.

16. The dispenser of claim The dispenser of claim 15, wherein the nozzle portion includes a plunger cavity that is laterally offset from the syringe dispensing end receiving cavity, the plunger cavity in fluid communication with the fluid flow path, the plunger cavity axially aligned with the measuring cavity, the tip portion of the dispenser plunger being positioned within the plunger cavity in the retracted state.

17. The system of claim 11, wherein the plunger includes a tip portion having an outer peripheral shape and the measuring cavity has an inner peripheral shape that corresponds to the outer peripheral shape of the tip portion.

18. The system of claim 17, wherein the outer peripheral shape of the tip portion is cylindrical with a first diameter and the inner peripheral shape of the measuring cavity is cylindrical with a second diameter, the first and second diameters being substantially identical.

19. The dispenser of claim 17, wherein the nozzle portion includes a plunger cavity in fluid communication with the fluid flow path, the plunger cavity axially aligned with the measuring cavity, the tip portion of the dispenser plunger being positioned within the plunger cavity in the retracted state.

20. A method of dispensing a predetermined amount of material comprising:
providing a prefilled syringe, the prefilled syringe includes:
a syringe body for storing the material; and a syringe plunger mounted within the syringe body for pressing the material out of the syringe body through a dispensing end of the syringe, providing a dispenser comprising:

a dispenser body including:

a syringe mounting region configured for receiving the syringe;

a nozzle portion having a syringe dispensing end receiving cavity configured to mate with the dispensing end of the syringe and an outlet, the nozzle portion defining a fluid flow path fluidly communicating the syringe dispensing end receiving cavity with the outlet, the outlet fluidly communicating the fluid flow path with the environment external to the nozzle portion, the fluid flow path including a measuring cavity having a predetermined volume; and a dispenser plunger carried by the dispenser body having a retracted state in which the dispenser plunger is retracted from the measuring cavity such that the outlet is in fluid communication with the syringe dispensing end receiving cavity and a depressed state in which the dispenser plunger extends through the measuring cavity, the dispenser plunger evacuating material within the measuring cavity as the dispenser plunger transitions from the retracted state to the depressed state;

actuating the syringe plunger to dispense material from the syringe body and through the fluid flow path until a portion of the material exits the outlet and to fill the measuring cavity with the dispenser plunger in the retracted state;

removing the portion of the material that exits the outlet; and depressing the dispenser plunger to transition the dispenser plunger from the retracted state to the depressed state to dispense the material from the measuring cavity.

* * * * *